United States Patent [19]

Fráter et al.

[11] 4,067,910

[45] Jan. 10, 1978

[54] PROCESS FOR MAKING ALLYLMERCAPTAN

[75] Inventors: Georg Fráter, Greifensee; Trudi Sigg-Grütter, Winterthur; Jost Wild, Porrentruy, all of Switzerland

[73] Assignee: Givaudan Corporation, Clifton, N.J.

[21] Appl. No.: 738,209

[22] Filed: Nov. 3, 1976

Related U.S. Application Data

[62] Division of Ser. No. 675,002, April 8, 1976, abandoned.

[30] Foreign Application Priority Data

Apr. 14, 1975 Switzerland .................... 4645/75
Feb. 25, 1976 Switzerland .................... 2318/76

[51] Int. Cl.² ................ C07C 149/08; C07C 149/26

[52] U.S. Cl. ................ 260/609 R; 560/266; 560/264; 560/103; 560/106; 260/514 J; 260/526 S; 260/609 D; 252/522; 426/535; 260/455 B

[58] Field of Search ............ 260/609 R, 455 B, 609 D

[56] References Cited

U.S. PATENT DOCUMENTS

2,101,649   2/1937   Groll ........................... 260/455 B

OTHER PUBLICATIONS

Reid, *Organic Chemistry of Bivalent Sulfur*, vol. I, p. 31.

*Primary Examiner*—Joseph Paul Brust
*Assistant Examiner*—Molly C. Eakin
*Attorney, Agent, or Firm*—Thomas Cifelli, Jr.; Robert F. Tavares

[57] ABSTRACT

Certain allylmercaptans, some of which are novel, can be used to make novel flavorant and fragrance compositions. A novel method for making the allylmercaptans is disclosed.

3 Claims, No Drawings

PROCESS FOR MAKING ALLYLMERCAPTAN

This is a division, of application Ser. No. 675,002 filed Apr. 8, 1976, now abandoned.

This invention relates to the fragrance and flavor fields and to novel allylmercaptans.

SUMMARY OF THE INVENTION

The present invention is concerned with a process for the manufacture of allylmercaptans. The invention is also concerned with certain of said allylmercaptans per se. The invention is further concerned with fragrant or flavoring compositions containing said novel allylmercaptans and with a method of imparting an odor or flavor to materials by means of said compositions or said novel allylmercaptans.

DESCRIPTION OF THE PREFERRED EMBODIMENTS

In accordance with the process provided by the present invention, allylmercaptans are manufactured by heating an allyl xanthogenate in an aqueous medium.

According to a particular embodiment of the present invention, an allyl xanthogenate of the general formula

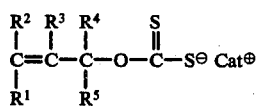

, wherein $R^1$, $R^2$, $R^3$, $R^4$ and $R^5$ each individually represent a hydrogen atom or a lower alkyl, lower alkenyl, lower alkynyl, lower cycloalkyl or lower cycloalkenyl group which may carry an oxygencontaining substituent, or $R^2$ and $R^3$ or $R^2$ and $R^4$ or $R^3$ and $R^4$ can be joined together to form a ring, and Cat+ denotes the cation of a base.
is heated in an aqueous medium to give a mixture of an allylmercaptan of the general formula

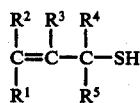

where $R^1$, $R^2$, $R^3$, $R^4$ and $R^5$ have the significance given earlier.
and an allylic rearrangement product thereof of the general formula

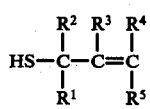

wherein $R^1$, $R^2$, $R^3$, $R^4$ and $R^5$ have the significance given earlier.

The finding that the heating of an allyl xanthogenate of formula II in an aqueous medium yields a mixture of an allylmercaptan of formula Ia and an allylic rearrangement product thereof of formula Ib is surprising since it was to be expected that, on heating the allyl xanthogenates, a decomposition into carbon disulphide and the allyl alcohol corresponding to the allyl xanthogenate would occur.

Examples of groups denoted by $R^1$, $R^2$, $R^3$, $R^4$ and $R^5$ are especially straight-chain or branched-chain alkyl, alkenyl or alkynyl groups containing up to 6 carbon atoms such as methyl, ethyl, propyl, isopropyl, butyl and isobutyl. $R^1$ may also represent, in particular, a group of the formula

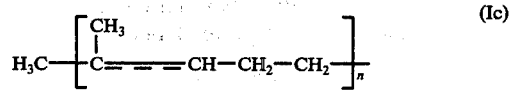

wherein $n$ stands for 1,2 or 3 and the broken line denotes an optional carbon-carbon bond.

Other examples of groups denoted by $R^1$, $R^2$, $R^3$, $R^4$ and $R^5$ are groups of the previously mentioned type carrying an oxygen-containing substituent such as a free, esterified or etherified hydroxy group, an oxo group or a froe or esterified carboxyl group. Esterified hydroxy groups are, for example, acyloxy groups containing acyl moieties derived from a lower aliphatic carboxylic acid such as formic acid, acetic acid, propionic acid, butyric acid etc or from an aromatic carboxylic acid such as benzoic acid. Etherified hydroxy groups are especially lower alkoxy groups such as methoxy, ethoxy, propoxy, isopropoxy etc, or aryloxy groups such as phenoxy etc. Examples of esterified carboxyl groups are carbalkoxy groups containing alkyl moieties derived from a lower alkanol such as methanol, ethanol, propanol etc. Further examples of groups denoted by $R^1$ are lower cycloalkyl groups (e.g. cyclopentyl or cyclohexyl) or lower cycloalkenyl groups (e.g. cyclopentenyl or cyclohexenyl) as well as such groups carrying an oxygen-containing substituent such as an aforementioned free, etherified or esterified hydroxy group or a free or esterified carboxyl group.

As mentioned earlier, $R^2$ and $R^3$, or $R^3$ and $R^4$, or $R^2$ and $R^4$ can also be joined together to form a ring. Examples of such rings are, in particular, carbocyclic 5-membered and 6-membered rings. Thus, for example, $R^2$ together with $R^3$ or $R^3$ together with $R^4$ or $R^2$ together with $R^4$ can represent a tetramethylene or pentamethylene group. These rings can, in turn, carry further substituents; for example, methyl, isopropyl, isopropenyl or like groups, or can also carry bridging elements such as, for example, methylene groups. Thus, it will be appreciated that the allylmercaptans of formula Ia and their allylic rearrangement products of formula Ib can have a p-menthane, thujane, carane, pinane, bornane (camphane) or like structure.

The bases yielding the cation denoted by Cat+ are expediently alkali metal hydroxides such as sodium hydroxide or potassium hydroxide, alkaline earth metal hydroxides such as magnesium hydroxide, alcoholates such as sodium methylate, sodium ethylate, potassium methylate, potassium ethylate etc, alkali metal hydrides such as sodium hydride etc, alkaline earth metal hydrides such as calcium hydride etc, metal alkyls such as butyllithium etc or metal aryls such as phenyllithium etc.

The heating of an allyl xanthogenate in accordance with the process provided by the present invention is expediently carried out at a temperature of from about 40° to about 100° C, preferably at about 80° to about 100° C.

The isolation of the products can be carried out in the usual manner; for example, by cooling the mixture obtained after the heating, neutralisation with acid and extraction with ether.

The separation of the mixture of an allylmercaptan of formula Ia and an allylic rearrangement product thereof of formula Ib into the individual components can be carried out by distillation.

The compounds of formulae Ia and Ib hereinbefore, certain of which are known and certain of which are novel, possess valuable organoleptic properties.

Known compounds are, for example, thiogeraniol and thiolinalool (see Belgian Pat. No. 784 016 and German Offenlegungsschrift No. 2 404 154).

Of the novel compounds, there are especially prominent 2-methyl-hept-2-ene-1-thiol, 2-methyl-hept-1-ene-3-thiol, 1-[1,1,3-trimethyl-3-cyclohexen-2-yl]-but-2-ene-1-thiol, 1-[1,1,3-trimethyl-3-cyclohexen-2-yl]-but-1-ene-3-thiol, 2-isopropyl-5-methyl-cyclohex-2-ene-1-thiol, 3,7,11-trimethyl-dodeca-1,6,10-triene-3-thiol, 3,7,11-trimethyl-dodeca-2,6,10-triene-1-thiol, oct-1-ene-3-thiol and oct-2-ene-1-thiol.

The novel compounds of formulae Ia and Ib possess particular odorant and/or flavouring properties and can accordingly be used in odorant and/or flavouring compositions, especially those having berry, fruit and/or flower notes.

Because of their interesting aroma properties, the compounds of formulae Ia and Ib manufactured in accordance with the process of this invention, can be used in the manufacture of high grade fruit aromas for foods (e.g. milk products, yoghurt etc), luxury goods (e.g. confectionery products such as bonbons) and drinks (e.g. table-water, mineral water etc). Their pronounced aromatic qualities enable them to be used in low concentrations (e.g. in the range of 0.1 ppm to 10 ppm, preferably in the range of 1 to 10 ppm). They can, however, also be used in higher concentrations (e.g. 50 ppm). Thus, for example, a mixture of 3,7,11-trimethyl-dodeca-1,6,10-triene-1-thiol and its allylic rearrangement products 3,7,11-trimethyl-dodeca-1,6,10-triene-3-thiol in the ratio of ca 1:1 can be used for the improvement of flavour properties (e.g. of citrus aromas such as grapefruit aromas) or of fruit juices, mineral waters etc having such prevailing flavour. In this case, in particular, the character of the grapefruit peel is emphasised in a desirable manner and the fruit character becomes balanced.

The novel compounds of formulae Ia and Ib also show advantageous properties in odorant compositions (e.g. in compositions having flowery notes) in that they are capable of modifying the odour of such compositions in a desirable manner. They can accordingly also be used as odorants for the production of perfumes, especially those having wood and flower notes, whereby the amount of a novel compound of formula Ia or Ib present can lie in the range of from about 0.001 wt.% to 5 wt.%, preferably from about 0.01 wt.% to 1 wt.%. In addition to their use as actual perfumes, such odorant compositions can also be used as bases for the perfuming of products such as solid and liquid detergents, synthetic washing agents, aerosols and cosmetic articles of all kinds (e.g. soaps, lotions, creams etc). The novel compounds of formulae Ia and Ib are also distinguished by an excellent tenacity.

3,7,11-Trimethyl-dodeca-1,6,10-triene-1-thiol or the allylic rearrangement product thereof is an especially interesting odorant. The use thereof comes into consideration, in particular, on the basis of the sulphur-like, fruity, metallic and green notes; for example, in odorant compositions having a flowery character (e.g. honeysuckle, orange blossom, tuberose etc).

It will accordingly be appreciated from the foregoing that the invention also includes within its scope (a) an odorant or flavouring composition which contains as an essential odour- or flavour-imparting ingredient a novel compound of formula Ia or Ib as hereinbefore set forth and (b) a method of imparting an odour or flavour to materials by incorporating therein or applying thereto an odour- or flavour-imparting amount of a composition defined under (a) or of a novel compound of formula a or Ib as hereinbefore set forth.

The allyl xanthogenates of formula II hereinbefore can be prepared by converting an allyl alcohol or the general formula

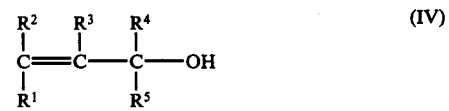

(IV)

wherein $R^1$, $R^2$, $R^3$, $R^4$ and $R^5$ have the significance given earlier,
into an alcoholate of the general formula

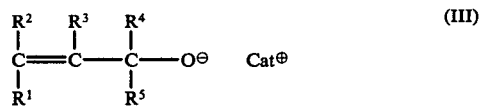

(III)

wherein $R^1$, $R^2$, $R^3$, $R^4$, $R^5$ and Cat+ have the significance given earlier,
and reacting said alcoholate with carbon disulphide.

The conversion of an allyl alcohol of formula IV into an alcoholate of formula III can be carried out according to methods known per se using one of the aforementioned bases. The conversion can be carried out in the presence of a solvent such as an ether (e.g. dimethyl ether, diethyl ether or tetrahydrofuran). The presence of a solvent is, however, not compulsory.

The reaction of an alcoholate of formula III with carbon disulphide can be carried out according to methods which are customary for the preparation of xanthogenates. Thus, for example, an alcoholate of formula III can be combined with carbon disulphide at a temperature of about −20° to +40° C, especially at 10° to 30° C. If the alcoholate formation has already been carried out in the presence of a solvent, the addition of a solvent is not necessary. However, if the alcoholate formation has been carried out in the absence of a solvent, it is expedient to add a solvent such as one of the aforementioned solvents.

The allyl xanthogenate of formula II forms as a precipitate which can be isolated by filtration and washing.

The following Example illustrates the process provided by the present invention:

EXAMPLE

Method A 0.1 mol of the allyl alcohol of formula IV is treated at 0°-20° C with 0.05 mol of powdered potassium hydroxide and the mixture is stirred for 30 minutes at 20° C and subsequently for 1 hour at 90° C. After cooling to 20° C, 0.06 mol of carbon disulphide and 100 ml of ether are added.

the precipitated allyl xanthogenate of formula II is filtered off, rinsed with ether, treated with a 10-fold amount of water and heated at 100° C under a nitrogen atmosphere for 1 hour. The mixture obtained is cooled, neutralised with acid and extracted three times with ether. The combined organic phases are washed with water, dried over anhydrous sodium sulphate and evaporated. There is thus obtained a mixture of the isomeric allylmercaptans of formulae Ia and Ib which, if desired, may be separated by distillation.

Method B 0.1 mol of the allyl alcohol of formula IV in 50 ml of dimethoxyethane is treated with 1.1 equivalents of sodium hydride and the mixture is heated at 50° C for 1 hour. After cooling the mixture, 1.5 equivalents of carbon disulphide are added and the mixture is stirred for a further 1 hour. The mixture is evaporated in vacuo.

The allyl xanthogenate of formula II obtained as the residue is heated at 100° C with a 10-fold amount by weight of water for 60 minutes. The working-up is carried out as described in Method A.

| Method | Allyl alcohol | Xanthogenate (II) / Water | Allylmercaptan (proportion of isomers) | |
|---|---|---|---|---|
| A | IV-1 | 1:50 | Ib-1 (72.5) | Ia-1 (25.2); Ia-1' (2.2) |
| A | IV-2 | 1:50 | Ib-2 (68.5) | Ia-2 (3); Ia-2' (13.8) |
| A | IV-3 | 1:10 | Ib-3 (40) | Ia-3 (60) |
| A | IV-4 c/tr | 1:10 | Ib-4 (85) | c/tr Ia-4 (15) |
| A | IV-5 | 1:10 | Ib-5 (90) | Ia-5 (10) |
| A | IV-6 | 1:10 | Ib-6 (95) | Ia-6 (5) |
| A | IV-7 | 1:10 | Ib-7 (45) | Ia-7 (55) |
| B | IV-8 | 1:10 | Ib-8 (60) | Ia-8 (40) |
| B | IV-9 cis-carveol (≈10% trans) | 1:10 | Ib-9 (~10% trans) | |

-continued

| Method | Allyl alcohol | Xanthogenate (II) / Water | Allylmercaptan (proportion of isomers) | |
|---|---|---|---|---|
| B | IV-10 | 1:10 | Ib-10 (15) | Ia-10 (85) |
| B | IV-11 | 1:10 | Ib-11 (~10% trans) | |
| B | IV-12 | 1:10 | Ib-12 (40) | Ia-12 (60) |
| B | IV-13 myrtenol | 1:10 | Ib-13 (70) | Ia-13 (30) |

The following Example illustrates a typical odorant composition containing the novel compounds of formula Ia and Ib provided by this invention:

Example

| Perfume composition (base) | Parts by weight |
|---|---|
| Myraldyl acetate | 300 |
| Linalyl acetate (synthetic) | 280 |
| Geraniol extra | 200 |
| Amyl salicylate | 100 |
| Styrallyl acetate | 20 |
| Methyl-3-heptenone-5-oxime (10% in ethanol) | 20 |
| | 920 |

By the addition of 80 parts by weight of 3,7,11-trimethyl-dodeca-1,6,10-triene-1-thiol and 3,7,11-triemthyl-dodeca-1,6,10-triene-3-thiol in the ratio of ca 1:1 to the foregoing composition, the final complex is intensified in a desirable manner. The fresh-flowery effect now becomes pronounced.

The terms "aroma" and "aromatic", as used herein include "flavor" and "flavorant", respectively, wherever the context so admits or requires.

The terms "odour" and "odourant", as used herein, mean "fragrance" and "fragrant", respectively, wherever the context so admits or requires.

What we claim is:

1. A process for the manufacture of allylmercaptans, which process comprises heating an allyl xanthogenate of the formula:

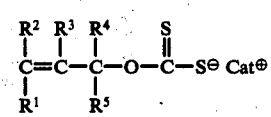

wherein $R^1$, $R^2$, $R^3$, $R^4$ and $R^5$ each independently represent a hydrogen atom or a lower alkyl, lower alkenyl, lower alkynyl, lower cycloalkyl or lower cycloalkenyl group which may carry an oxygen-containing substituent, or $R^2$ and $R^3$ or $R^2$ and $R^4$ or $R^3$ and $R^4$ can be joined together to form a ring, and Cat+ denotes the cation of a base selected from the group consisting of alkali metal hydroxides, alkaline earth metal hydroxides, alcoholates, alkali metal hydrides, alkaline earth metal hydrides, metal alkyls and metal aryls, in an aqueous liquid medium to give a mixture of an allylmercaptan of the general formula

wherein $R^1$, $R^2$, $R^3$, $R^4$ and $R^5$ have the significance given earlier in this claim, and an allylic rearrangement product thereof of the general formula

wherein $R^1$, $R^2$, $R^3$, $R^4$ and $R^5$ have the significance given earlier in this claim, the ratio of allyl xanthogenate to liquid being from about 1:10 to 1:50.

2. A process according to claim 1, wherein the allyl xanthogenate is heated at a temperature of from about 40° to about 100° C.

3. A process according to claim 1, wherein the resulting mixture of allylmercaptan and its allylic rearrangement product is separated by distillation.

* * * * *